US012596088B2

(12) United States Patent
Lepple-Wienhues

(10) Patent No.: US 12,596,088 B2
(45) Date of Patent: Apr. 7, 2026

(54) ELECTROCHEMICAL PROBE

(71) Applicant: Merck Patent GmbH, Darmstadt (DE)

(72) Inventor: Albrecht Lepple-Wienhues, Les Charbonieres (CH)

(73) Assignee: Merck Patent GmbH, Darmstadt (DE)

( * ) Notice: Subject to any disclaimer, the term of this patent is extended or adjusted under 35 U.S.C. 154(b) by 142 days.

(21) Appl. No.: 18/692,157

(22) PCT Filed: Sep. 15, 2022

(86) PCT No.: PCT/EP2022/075629
§ 371 (c)(1),
(2) Date: Mar. 14, 2024

(87) PCT Pub. No.: WO2023/041635
PCT Pub. Date: Mar. 23, 2023

(65) Prior Publication Data
US 2024/0426773 A1     Dec. 26, 2024

(30) Foreign Application Priority Data
Sep. 17, 2021    (EP) ..................................... 21197369

(51) Int. Cl.
*G01N 27/30*        (2006.01)
*G01N 27/38*        (2006.01)
(Continued)

(52) U.S. Cl.
CPC ........... *G01N 27/301* (2013.01); *G01N 27/38* (2013.01); *G01N 27/401* (2013.01); (Continued)

(58) Field of Classification Search
CPC .... G01N 27/301; G01N 27/38; G01N 27/414; G01N 27/4163; G01N 27/403; G01N 27/401; G01N 33/4836
See application file for complete search history.

(56) References Cited

U.S. PATENT DOCUMENTS 4,012,325 A * 3/1977 Columbus ........... B01L 3/50215
                                                    422/918
4,437,970 A * 3/1984 Kitajima .............. G01N 27/307
                                                    204/435
(Continued)

FOREIGN PATENT DOCUMENTS

DE          10351682 A1 * 7/2004    ............. G01N 27/27
EP          0299778 A2   1/1989
JP        2017-125822 A   7/2017

OTHER PUBLICATIONS

The New Zealand Journal of Medical Laboratory Technology, vol. 23, No. 1, Mar. 1969 (complete issue) (Year: 1969).*
(Continued)

*Primary Examiner* — Alexander S Noguerola
(74) *Attorney, Agent, or Firm* — Nields, Lemack & Frame, LLC

(57) ABSTRACT

Novel type of electrochemical probe comprising a reference electrode array, each reference electrode comprising a conductor element. The set-up allows for internal calibration as well as being adapted to long storage in dry state. Individual conductive elements of the electrode array do not start to shift/drift, simultaneously but that it is rather individual conductive elements that show deviating behavior. Relatively simple statistical analysis of the respective voltages obtained for the respective conductive elements of the reference electrode array allow identifying such deviating conductive elements, and then take corrective action, such as for example disregarding the measured values provided by such deviating conductive element or regenerating such deviating conductive elements by applying a voltage to re-chlorinate or electrochemical snibbing the surface of such element for cleaning purposes, which can also be done with the respective probe or reference electrode remaining in
(Continued)

place, i.e. without for example having to remove the junction element comprising the electrolyte.

16 Claims, 8 Drawing Sheets

(51) Int. Cl.
| | |
|---|---|
| *G01N 27/401* | (2006.01) |
| *G01N 27/414* | (2006.01) |
| *G01N 27/416* | (2006.01) |
| *G01N 33/483* | (2006.01) |

(52) U.S. Cl.
CPC ....... *G01N 27/414* (2013.01); *G01N 27/4163* (2013.01); *G01N 33/4836* (2013.01)

(56) References Cited

U.S. PATENT DOCUMENTS

| | | | | | |
|---|---|---|---|---|---|
| 4,613,421 | A | * | 9/1986 | Seshimoto | G01N 35/00029 |
| | | | | | 204/407 |
| 4,655,899 | A | * | 4/1987 | Saito | G01N 27/307 |
| | | | | | 204/412 |
| 5,004,998 | A | * | 4/1991 | Horii | G01N 27/403 |
| | | | | | 702/185 |
| 5,162,077 | A | * | 11/1992 | Bryan | G01N 27/38 |
| | | | | | 204/402 |
| 5,766,432 | A | * | 6/1998 | Dunn | A61B 5/1495 |
| | | | | | 204/406 |
| 11,280,755 | B2 | * | 3/2022 | Gish | G01N 27/3275 |

OTHER PUBLICATIONS

EPO machine-generated English language translation of Winfried Schelibach DE 10351682 A1, patent published Jul. 15, 2004 (Year: 2004).*

Leisure Pools, "Vinyl Ester Resin: The Secret Behind Stunning Fiberglass Pools," https://ourleisurepools.ca/pool-build/vinyl-ester-resin/, 2025 (Year: 2025).*

International Search Report and Written Opinion mailed Feb. 17, 2023 in corresponding PCT application No. PCT/EP2022/075629.

Desmond et al., Evaluation of miniaturised solid state reference electrodes on a silicon based component. Sensors and Actuators B. vol. 44, pp. 389-396, Oct. 1997.

* cited by examiner

Fig. 5 Part1
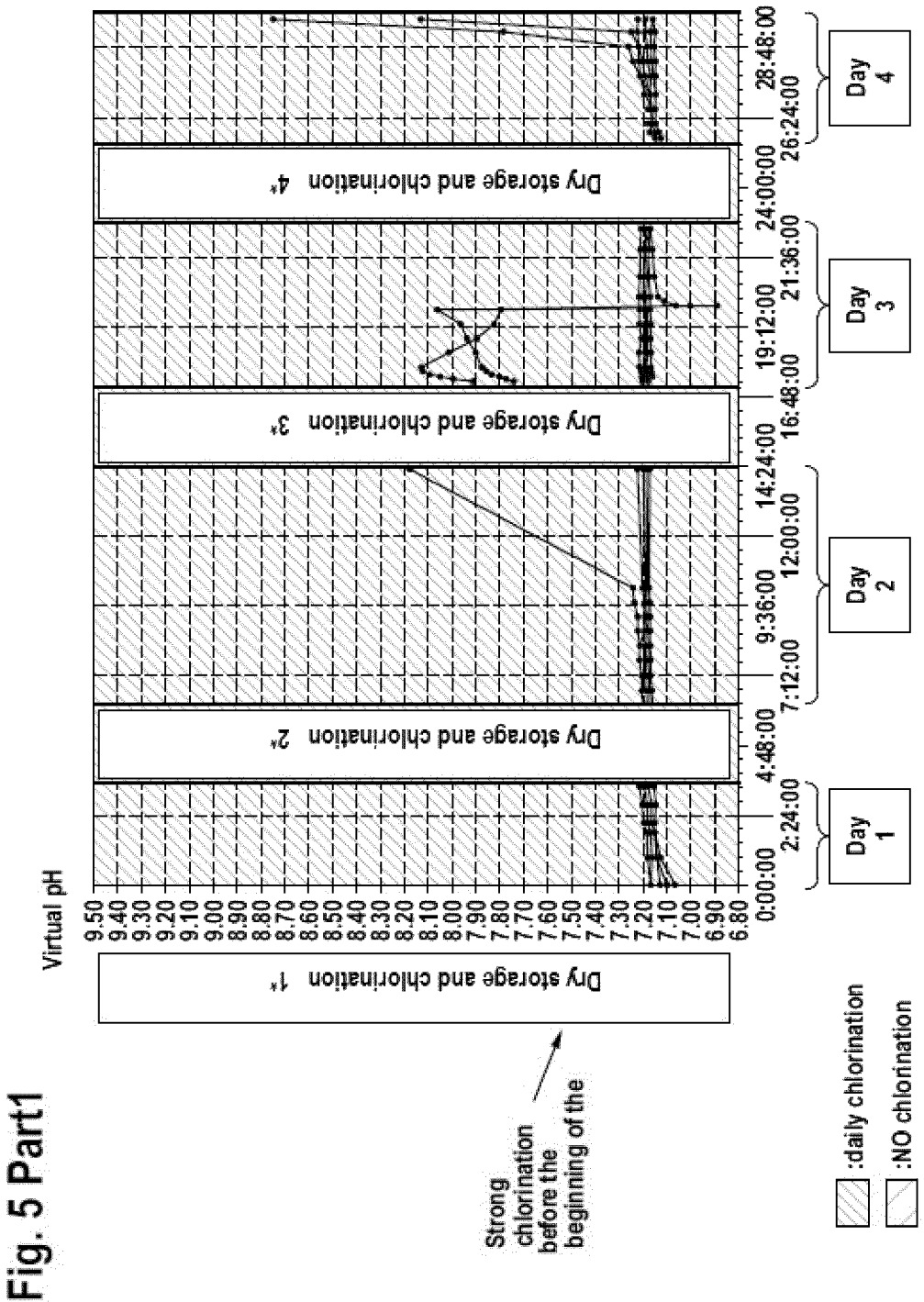

Fig. 5 Part 2
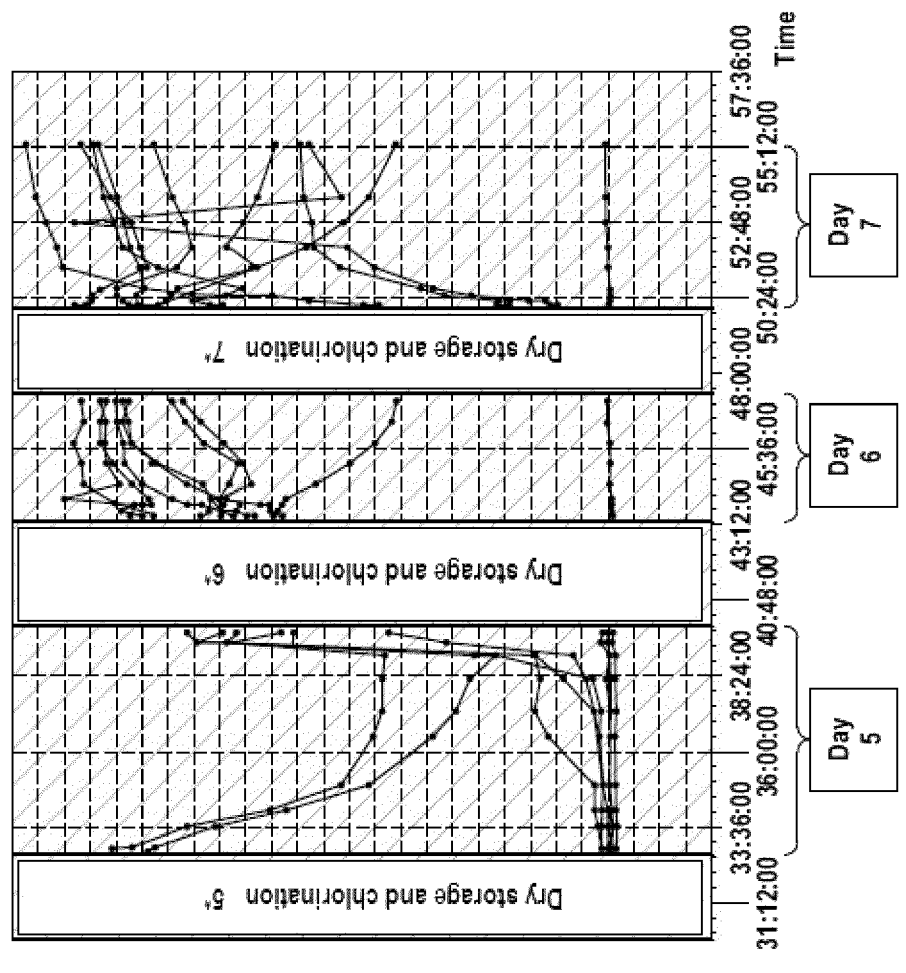
 :daily chlorination
:NO chlorination

Fig. 6 Part 1
Electrode Array A inter-electrode voltage deviation from array average (no reference electrode)
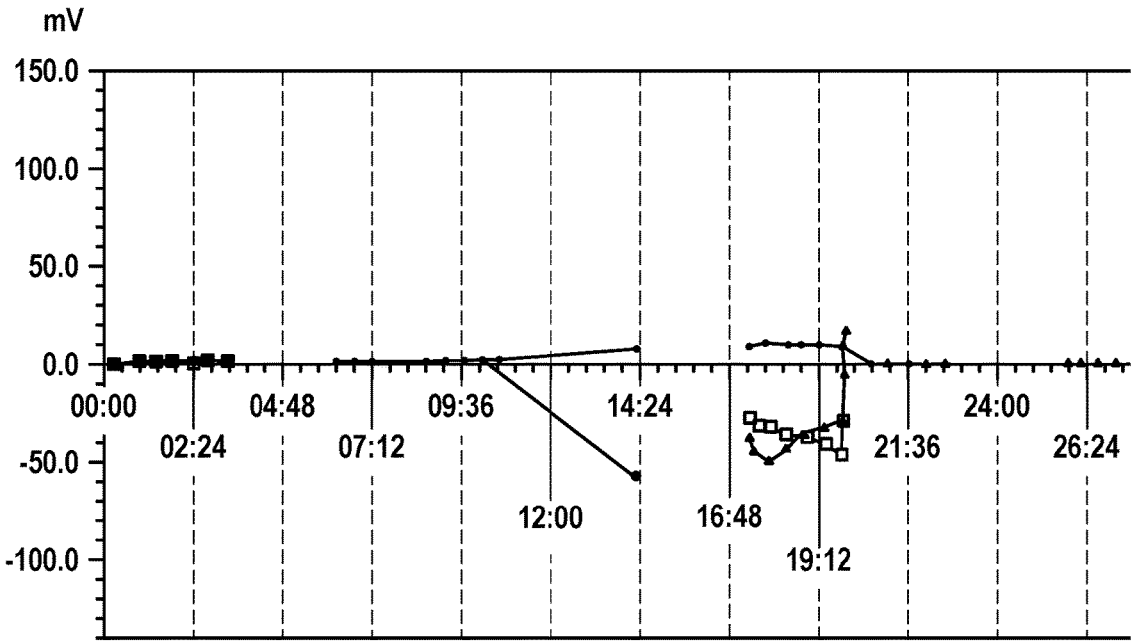
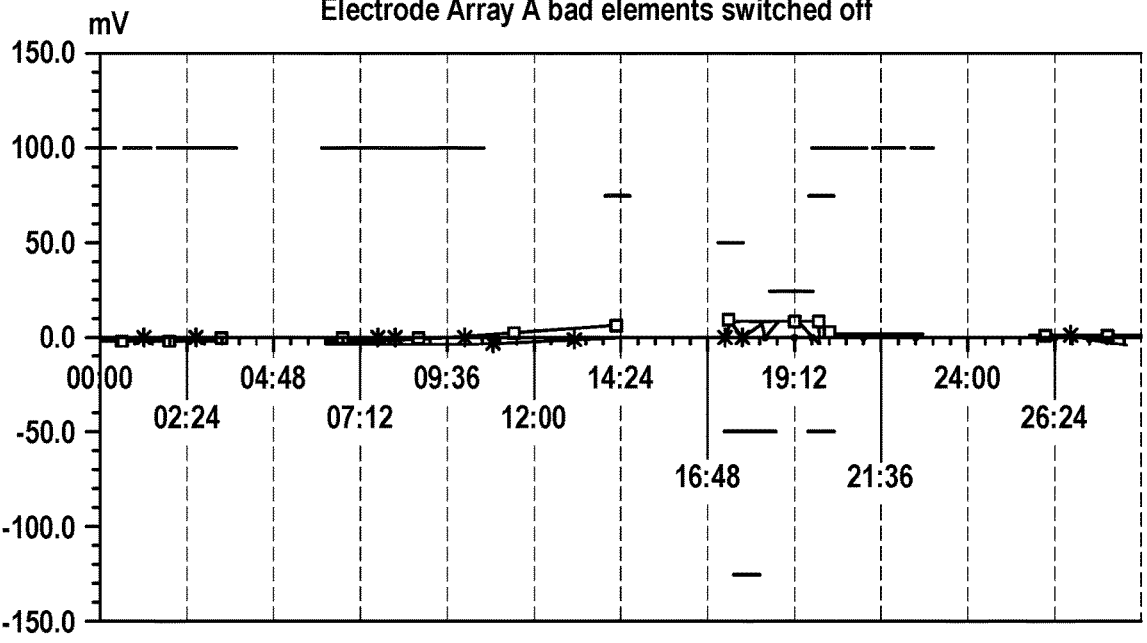
-O- Series1   -□- Series2   -◆- Series3   -△- Series4   -✳- Series5   -•- Series6   -O- Series7

Fig. 6 Part 2
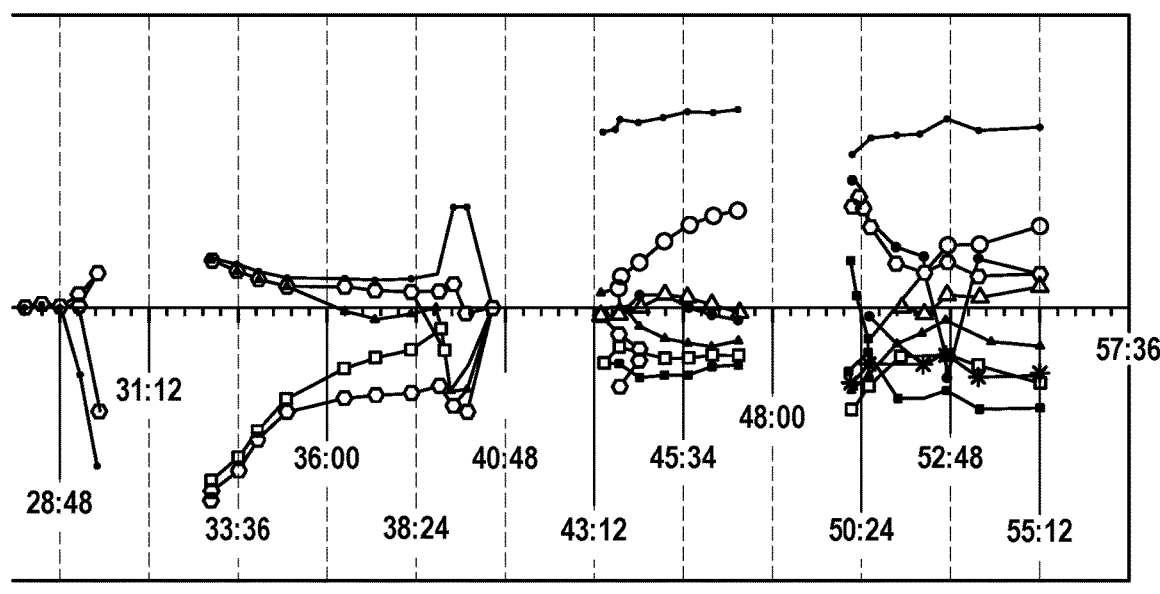
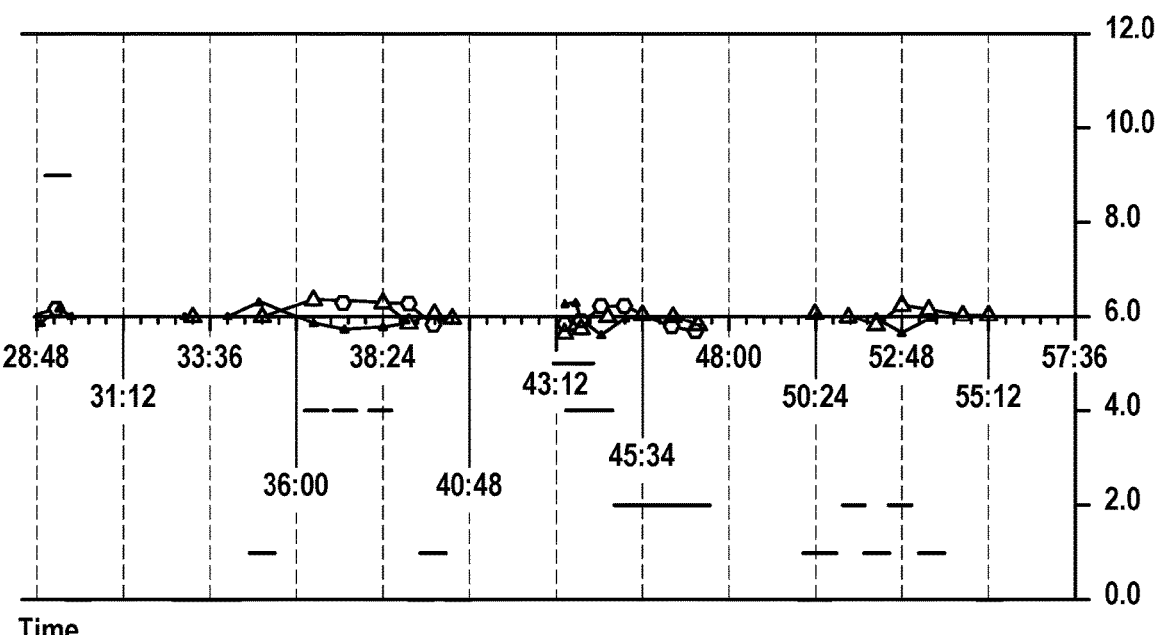
Time
—▲— Series8   —✳— Series9   —■— Series10   — Series11

ELECTROCHEMICAL PROBE

TECHNICAL FIELD

The present invention relates to a novel type of electrochemical probe allowing for internal calibration as well as being adapted to long storage in dry state.

BACKGROUND

Measurement of a liquid's characteristics such as pH, concentrations of other ions and solute concentrations are of interest in a wide variety of scientific, medical, industrial, commercial and domestic processes and situations.

Sensors for such measurements often operate on an electrochemical principle that incorporates a reference electrode (RE) and a sensing electrode, such sensing electrode being selected from the non-limiting group including electrochemical sensors, voltammetric sensors, potentiometric sensors and/or amperometric sensors.

Historically such electrochemical sensors, for example for pH measurement, have not been very user-friendly as they require intensive maintenance including wet storage, repeated calibration, frequent replacement of electrolytes, and chlorination. Even with this high usability burden, drifting out of calibration, for example due to a baseline drift, within short time had to be accepted by the users, necessitating frequent re-calibration.

Due to their ease of use, ion selective field effect transistors (ISFET) have now become an interesting alternative to the historically used sensors. However, they still require pairing with a reference electrode because the parameter to be measured is generally determined on basis of the potential difference between two electrodes, i.e. the measuring electrode (for example, an ISFET) and a reference electrode. From the point of electrochemistry, the thermodynamically defined, classical, or conventional, reference electrode is a special electrode (also called "half-cell") featuring a reversible electrode reaction and a stable electrolytic contact to the analyte. Such reversible reaction results in a distinct and stable electrode potential.

Conventional reference electrodes for use in such potentiometric electrochemical measurements typically incorporate an internal reference fill solution in contact with an electrode in turn in contact with a test solution through a porous junction or membrane, wherein the porous junction or membrane allows for a slow leak of the internal reference fill solution to provide the necessary electrolytic contact with the liquid being tested. A metal or electrochemical electrode, serving as sensing electrode, in contact with the test solution completes the circuit, and the electrical potential on the reference electrode remains relatively constant while the sensing electrode responds to chemical changes in the test solution.

The best known and most widely used reference electrodes are those comprising an inner element, which is generally silver/silver(I) chloride (Ag/AgCl) or mercury/mercury(I) chloride (Hg/Hg₂Cl₂), the latter frequently also referred to as calomel electrode. Of these, silver/silver(I) chloride reference electrodes are generally preferred and widely used due to their environmental compatibility. The mercury/mercury(I) chloride or calomel electrode has advantages regarding potential stability, but mercury presents severe environmental hazards and its use is generally restricted. As necessary component for them to be able to work, these reference electrodes commonly comprise "wet chemistry", generally in form of an aqueous electrolyte. As preferred example of such aqueous electrolyte, mention may be made of a saturated aqueous solution of potassium chloride since the ion mobilities of the potassium cations and the chloride ions are comparable, thus largely avoiding liquid junction potentials. Despite efforts to develop alternatives, the traditional, frequently rod-shaped or cylindrical REs are commercially still dominant.

Though a number of alternative approaches using solid-state reference electrodes, based for example on thick-film technology, ink-jet printing, thin-film technology, spraying, heat sealing, conducting polymers, semi-permeable membranes and microfabrication, has been reported, as disclosed for example in M. Sophocleous et al., Sensors and Actuators A 267 (2017) 106-120, or in I. Shitanda et al., Analyst, 2015, 140, 6481-6484, these have yet to achieve the same level of reliability as the conventional mercury/mercury(I) chloride or silver/silver chloride(I) reference electrodes.

Additionally, such solid-state REs generally suffer from leakage of water and ions from the electrolyte region and junction, causing the electrode potential to shift. Specifically, the smaller such REs are designed, the more pronounced the leakage and dilution out of the electrolyte region is.

Another big challenge is dry storage of reference electrodes. Since the known reference electrode technologies, including the currently known solid-state reference electrodes, require an electrolyte section, conventional mercury/mercury(I) chloride or silver/silver(I) chloride reference electrodes always need to be stored in saturated aqueous electrolyte solutions, such as a saturated aqueous solution of potassium chloride, while for solid-state reference electrodes evaporation of water during dry storage is unavoidable and can only be reduced, but never completely eliminated, by sealed compartment designs, which in turn create challenges regarding durability and contamination. Following dry storage, such solid-state reference electrodes require lengthy rehydration, and are generally found to be less stable than conventional reference electrodes.

There is therefore a general need, particularly in industry and research, to provide a reference electrode not suffering from the above-mentioned drawbacks.

It is therefore an object of the present application to provide an improved reference electrode.

It is also an object of the present application to provide a reference electrode that is characterized by one of the more of the characteristics selected from the group consisting of easier maintenance, improved dry storage capabilities, facilitated use, and stable potential.

SUMMARY

It has now been surprisingly found by the present inventors that the above objects may be attained either individually or in any combination by the present, preferably electrochemical or potentiometric, probe and the respective method of determining an ion concentration as well as by a vessel comprising such probe, and further by a system comprising such vessel.

The present application therefore provides a probe for the potentiometric measurements comprising
- an electrode array comprising at least two conductive elements electrically insulated against each other, and each conducting element exposing a conductive surface;
- a junction element comprising an absorbent material and an electrolyte, connecting the conductive surface of said conductive elements to a liquid;

a device ("measuring device") capable of measuring voltages between the conductive elements comprised in the electrode array; and means of electrically connecting the electrode array and the device.

Further preferred probes as defined herein may comprise—in a non-limiting way—one or more of the following features:

The electrode array comprises at least three, for example, four, five, six, seven, eight, nine, ten, eleven, or twelve, conductive elements.

The electrode array comprises at most twelve conductive elements.

The conductive elements comprise a conductive material selected from the group consisting of silver, gold, platinum, mercury, carbon and any blend of any of these, and preferably the conductive material is silver.

The conductive elements are pellet-shaped.

The absorbent material is either a porous material (preferably a filter paper) or a porous polymer.

The electrolyte is an alkaline metal chloride, preferably potassium chloride.

The device capable of measuring voltages is an electronic circuitry which is connected to and measuring voltage between the conductive elements.

The electronic circuitry can selectively address any one or more individual conductive element, and/or to selectively apply a current to any one or more individual conductive element.

The probe further comprises a controller unit that comprises one or more of the following features of (i) controlling the electronic circuitry, (ii) being capable of connecting and/or addressing the conductive elements either singly or in any combination, and (iii) being capable of identifying and/or dealing with any unstable ("deviating") conductive elements in the electrode array.

The controller deals with unstable ("deviating") conductive elements in the electrode array, for example by disregarding the respective voltage value obtained from such unstable conductive element and/or by restoring stability by selectively applying current with selected polarity to such at least one deviating conductive element for electrochemical scrubbing and coating, preferably by using dechlorination and/or chlorination.

The electrode array is immersed in an aqueous solution of the electrolyte.

The probe further comprises an electrochemical sensor, wherein the electrochemical sensor is preferably an ion-sensitive field-effect transistor (ISFET).

Additionally, the present application provides for a vessel comprising such probe.

The present application also provides for a system comprising such probe or such vessel, such system preferably being selected from the group consisting of a water purification system or a water solution preparation system, though it may, for example, also be used in food and beverage applications, for example, to in the determination of the pH of a sample.

Further, the present application provides for a method of determining an ion concentration in an aqueous medium, the method comprising in sequential order the following steps:

a) Submersing the present probe in any of the mentioned versions in water, and connecting it to the measuring device as defined herein;

b) taking a voltage measurement for each of the conductive elements of the electrode array by using said measuring device;

c) determining and eliminating any unstable conductive elements by using a data analysis device; and d) calculating an average voltage from the voltage measurements obtained for the non-deviating conductive elements by using the data analysis device;

Further preferred developments of the present method of determining an ion concentration in solution comprise the additional method steps of:

e) providing an electrochemical sensor as defined herein in an aqueous ion solution;

f) combining the conductive elements for which the average voltage has been calculated as a reference electrode by using the data analysis device; and g) subsequently taking a voltage measurement from the electrochemical sensor using the reference electrode from step (f);

wherein steps (a) to (f) may be performed in any order provided that (i) steps (a) to (d) are performed sequentially;

(ii) steps (f) and (g) are performed sequentially; and (iii) step (g) is performed after steps (a) to (f).

Such method may preferably further comprise the following steps of h) performing a statistical evaluation determining the stability of the electric potential of the array and its individual elements by analyzing the voltage readings obtained in step (b) above by using the data analysis device, and i) if at least one unstable ("deviating") conductive element is identified, selectively apply current with selected polarity to such at least one deviating conductive element for electrochemical scrubbing and coating, preferably using dechlorination and/or chlorination.

BRIEF DESCRIPTION OF THE DRAWINGS

FIG. 2 shows a schematic view of a cross-section of an exemplary reference electrode of the exemplary reference electrode array of FIG. 1a.

FIG. 5 shows the voltage curves for ten conductive elements of the electrode array of Example 1 in the simulation of a work week.

FIG. 6 shows the voltage for each of the individual conductive elements comprised in the electrode array of Example 2 and shows the average voltage of that electrode array with deviating conductive elements being disregarded.

5

6

Figures 1A, 1B:
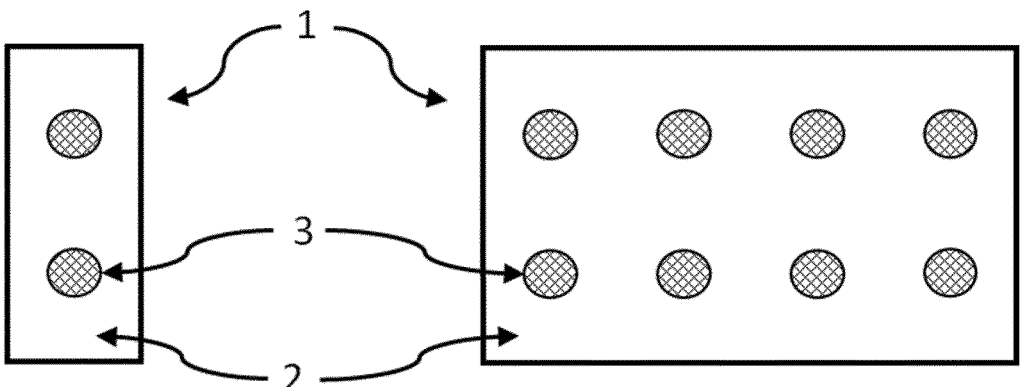
FIG. 1a shows a schematic top view of an exemplary electrode array as described herein comprising two conductive elements.
FIG. 1b shows a schematic top view of an exemplary electrode array as described herein comprising eight conductive elements.

In the drawings, the same reference numerals are to indicated corresponding elements/features.

DETAILED DESCRIPTION

As used herein, the term "substantially" is used to indicate a deviation or difference of ±10%, preferably of ±5%, and most preferably of ±1%, relative to the smallest of the compared values.

As used herein, the terms "isolate" and "insulate" and their respective derivatives are used synonymously.

As used herein, the terms "isolate", "insulate", and "connect" as well as their respective derivates are used in the sense of "electrically isolate/insulate/connect", unless indicated otherwise. For example, the term "conductive element" is used to denote an "electrically conductive element".

In general terms, the present, preferably electrochemical or potentiometric, probe comprises an electrode array, a junction element, a device capable of measuring voltages ("measuring device"), and means of electrically connecting ("connecting means") the electrode array and the measuring device.

Generally, the present probe may be used to determine ion concentrations, including pH-values, in aqueous medium.

The present electrode array comprises at least two conductive elements. Preferably, the present electrode array comprises at least three or four or five or six or seven or eight or nine or ten or eleven or twelve conductive elements. Though the maximum number of conducting elements comprised in the electrode array is not particularly limited, it is nevertheless preferred that the present electrode array comprises at most twelve conductive elements.

The conductive elements comprised in the electrode array are electrically isolated against each other, exposing a conductive surface. The exposed conductive surface may then be in contact with an environment, generally a liquid, such as an aqueous medium, for example an aqueous solution of the electrolyte used herein.

The shape of the conductive elements is not particularly limited. They may, for example, be of circular, oval, rectangular, square, pentagonal, hexagonal, octagonal, pellet, cylindrical, drop-like, or any other suitable shape. It is nevertheless preferred that they are circular, i.e. are pellet-shaped or cylindrical. The size of the conductive elements is not particularly limited. Preferably their longest dimension is at least 0.1 mm. Preferably their longest dimension is at most 1.0 cm (for example at most 9.0 mm or 8.0 mm or 7.0 mm or 6.0 mm or 5.0 mm), still even more preferably at most 4.0 mm or 3.0 mm or 2.0 mm, and most preferably at most 1.0 mm. Without wishing to be bound by theory, it is believed that the flexibility in terms of size renders the present conductive elements, and in consequence, the present electrode array, suitable for numerous applications, particularly for applications where a small size of the electrode array may be required (for example, in laboratory equipment).

Preferably, the conductive elements comprised in the electrode array are substantially of, preferably have, the same size, for example, have substantially the same exposed conductive surface area.

The present conductive elements thus preferably comprise, or most preferably consist of, an electrically conductive material. Preferably, such electrically conductive material is selected from the group consisting of carbon, metal, and metal alloy. Suitable metals may, for example, be selected from the group consisting of silver, gold, platinum, and mercury. Most preferably, the electrically conducting material is silver.

Preferably, the present conductive elements are comprised in/on a supporting base. Such supporting base preferably consists of an electrically non-conducting, i.e. isolating, polymer. Suitable examples of such electrically non-conducting polymer may be selected from the list consisting of polyolefins, such as propylene polymers, ethylene polymers, copolymers of ethylene and alpha-olefins (with such alpha-olefins being, for example, any one or more selected from the group consisting of propylene, butene, hexene and octene); silicones; styrene-comprising polymers, such as styrene homopolymer, acrylonitrile butadiene styrene (ABS); fluoropolymers, such as polytetrafluoroethylene (PTFE), polyvinylidene fluoride (PVDF), poly(hexafluoropropylene), and polyvinyl fluoride (PVF); poly(acrylic acid), polymethacrylate, polyamide, polyimide, polyurethane, polybenzimidazole, polycarbonate, polyacrylonitrile, poly(vinyl alcohol), poly(lactic acid), polyethylene oxide, polyaniline, polyethylene terephthalate, polybutylene terephthalate, poly(acryl amide), polycaprolactone, poly(ethylene co-vinyl alcohol), polysulfone (PSU), and polyethersulfone (PES).

Preferably, the supporting base—if present—may comprise walls, thus forming a tub. Without wishing to be bound by theory, it is believed that such a tub-shape further improves the reliability and accuracy of the present probe in that the tub-like shape helps in reducing convection in the environment, e.g. the aqueous medium, surrounding the present conductive elements, thus allowing for lower variation in the concentration of the aqueous solution of the present electrolyte in the proximity of the conductive elements.

FIGS. 1a and 1b show schematic top views of exemplary electrode arrays (1) as defined herein. Said electrode arrays (1) comprise a—as such non-essential for the functioning of the present probe—supporting base (2) as well as two (FIG. 1a) and eight (FIG. 1b) conductive elements (3).

The present junction element as comprised in the probe as defined herein comprises an absorbent material and an electrolyte. The junction element serves to establish a liquid connection between the exposed conductive surfaces of the conductive elements described herein with an environment, which is generally a liquid, such as an aqueous medium. The junction element is preferably located in proximity of the conductive elements comprised in the electrode array, for example more or less directly above these.

Preferably, the absorbent material is a porous material. Suitable examples of porous materials may be selected from the group consisting of filter paper and porous polymers. The preferred absorbent material is a filter paper.

Preferably, the electrolyte is a metal salt. Preferred metal salts are halides. More preferred are alkaline metal halides and earth alkaline metal halides. Suitable examples of such halides may be selected from the group consisting of lithium halides, sodium halides, potassium halides, rubidium halides, beryllium halides, magnesium halides, calcium halides, and strontium halides. Preferred halides are chlorides. Most preferred electrolyte is potassium chloride.

For reasons of clarity it is noted that when in the dry state the junction element comprises the electrolyte as a metal salt. When in use or being prepared for use the junction element is immersed in water, thus dissolving the metal salt at least partially, consequently leading to a saturated aqueous metal salt solution around the junction element, and due to the junction element being in proximity to the conductive elements comprised in the electrode array also around these conductive elements.

The device capable of measuring voltages between the conductive elements comprised in the electrode array (this device also referred to as "measuring device" or "voltmeter" throughout the present application) is preferably an electronic circuitry, which is connected to and measuring the voltages of the conductive elements. Preferably, said measuring device is connected to each conductive element individually.

The present probe consequently also comprises means for connecting ("connecting means") the electrode array and the measuring device. Preferably, these connecting means connect the measuring device individually to each conductive element of the electrode array. Preferably such connecting means is a wire, particularly an electrically conductive wire.

Figure 2:
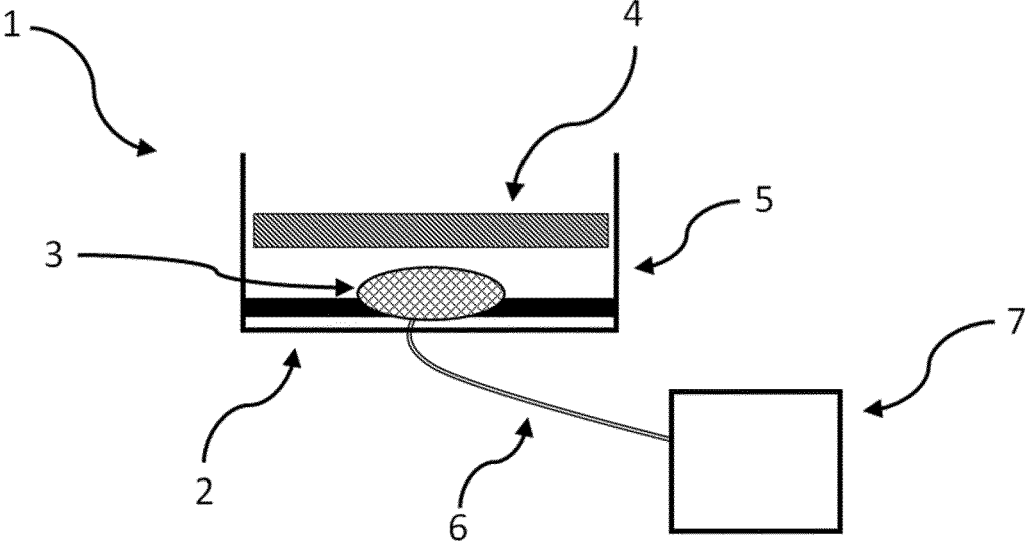

A schematic view of a cross-section of the exemplary reference electrode of FIG. 1a is shown in FIG. 2, wherein electrode array (1), which comprises a supporting base (2) with side walls (5), a conductive element (3) and a junction element (4), is connected to a measuring device (7) by connecting means (6) such as a wire.

Figure 3:
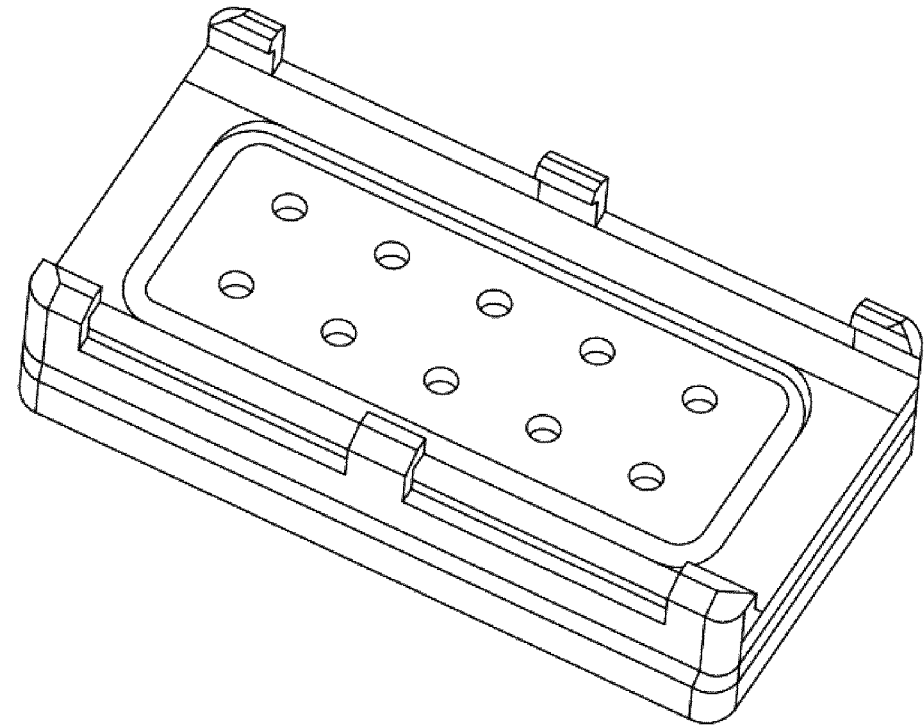
FIG. 3 shows an exemplary perspective illustration of an exemplary electrode array as described herein comprising ten conductive elements.

A schematic perspective representation of an exemplary electrode array as defined herein is shown in FIG. 3, with the electrode array being shown as comprising ten conductive elements.

Taken together, the electrode array, the junction element, the measuring device, and the means of connecting the electrode array and the measuring device may also be seen as constituting a reference electrode. Said reference electrode may then be comprised by the probe as defined herein. Thus, the present probe may be seen as comprising a reference electrode, the reference electrode in turn comprising the electrode array, the junction element, the device capable of measuring voltages, and the means of connecting the electrode array and the device capable of measuring voltages Thus, the present application discloses a probe comprising a reference electrode as defined herein for one or more electrochemical sensor as well as a method of using such reference electrode and probe for determining an ion concentration in a, preferably aqueous, solution. Preferably, in a preferred exemplary embodiment the present probe comprises one or more of the following features:

A re-useable electrode array comprising at least two conductive elements, the conductive elements preferably in form of pellets, and/or preferably made from silver (Ag);

a disposable junction element comprising an absorbent material, preferably a filter paper, and an electrolyte, the electrolyte preferably being potassium chloride (KCl);

an electronic circuitry connected to and measuring voltages between the conductive elements comprised in the electrode array, to allow selectively addressing any one or more individual conductive element comprised in the electrode array, and/or to selectively apply a current to any one or more individual conductive element, preferably for electrocoating silver pellets with silver(I) chloride (AgCl); and a control circuit monitoring conductive element voltage stability, identifying and disregarding any deviating conductive element in measurements, and restoring conductive element stability by selective chlorination thereof.

Preferably, the probe or the reference electrode as defined herein also comprises means ("data analysis means") for statistical analysis of the voltages obtained by the measuring device. The data analysis means is capable of and adapted to identify any deviating conductive element and to calculate an average reference voltage for the non-deviating conductive elements. Such statistical analysis is performed as described in detail in the following.

Preferably, the probe or the reference electrode as defined herein, also comprises means ("reference electrode current controller" or "RE current controller") for selectively applying current to one or more individual conductive element or to all conductive elements comprised in the electrode array as defined herein. Such application of a current is described in detail in the following.

Preferably, the present probe also comprises a sensing electrode. Said sensing electrode is capable of or adapted to provide a current/voltage that is proportional to the ion concentration in the liquid, preferably the liquid being an aqueous medium comprising dissolved ions.

Such sensing electrode, also referred to as "electrochemical sensor" in the present application, is preferably an ion-sensitive field-effect transistor ("ISFET"). An ISFET may be used to measure ion concentrations in solution, preferably an aqueous solution. With changing ion concentration, such as for example $H^+$, the current through the transistor will change accordingly.

The structure of an ion-sensitive field-effect transistor essentially corresponds to that of a field-effect transistor (FET), wherein, however, the gate is formed by (i) the solution comprising the to-be-analysed ion, and (ii) an ion-sensitive or ion-selective membrane, deposited onto the gate insulator and in direct contact with the solution.

The conductivity between source and drain electrode, which in a FET is determined by the voltage of the gate, in an ISFET is controlled by chemical processes at the surface of the gate insulator. Exemplary gate insulator materials may be selected from the group consisting of $SiO_2$, $Si_3N_4$, $Al_2O_3$, and $Ta_2O_5$.

Such ion-sensitive field-effect transistors are well known to the person skilled in the art and are commercially available from various sources. As example of a commercially available ion-sensitive field-effect transistor mention may be made of the MSFET-3330 pH sensor, available from Microsens SA, Lausanne, Switzerland.

Preferably, the present probe further comprises a device capable of calculating a value for the ion concentration on basis of the average reference voltage provided by the data analysis means and the voltage provided by the sensing electrode, such concentration value then being transferred via an output device to a further controller, to a recorder, to a display, or any other suitable means.

The probe or reference electrode as defined herein may be comprised in any volume holding or conveying or adapted to hold or adapted to convey a liquid, preferably an aqueous medium. Such volume is not limited to any specific type or shape, provided that it is capable of holding or transferring a liquid. Such volume may be any selected from the group consisting of vessel, conduit, flow cell, flow-through cell, flow reactor, flow-through reactor and any similar. Suitable examples may be selected from the non-limiting group consisting of vessel, bottle, box, silo, dispenser, intermediate bulk container (IBC), tank, drum, bowl, cup, container, tube or pipe.

Such vessel or conduit may be comprised in a system. The type of system is not particularly limited. The present probe or reference electrode may be used in any system where the determination of an ion concentration may be required. Non-limiting examples of such a system may be selected from the group consisting of water purification systems, and water solution preparation systems.

It is noted that the architecture and/or layout and/or organization of the measuring device, the data analysis device, the reference electrode current controller, the calculation device, and the output device is not particularly limited and may be adapted to be best suited to the specific purpose and application. For example, the measuring device, the data analysis device, the reference electrode current controller, the calculation device, and the output device may all be included into one single probe controller, or may be comprised in different devices. For example, the measuring device, the data analysis device, and the reference electrode current controller may be comprised in a reference electrode controller. For example, the calculation device, and the output device may be included in a sensor controller. Each of these devices and/or controllers may be an electronic circuitry, or may be, for example, a computer capable of performing the necessary tasks and process steps as described in the following.

Figure 4:
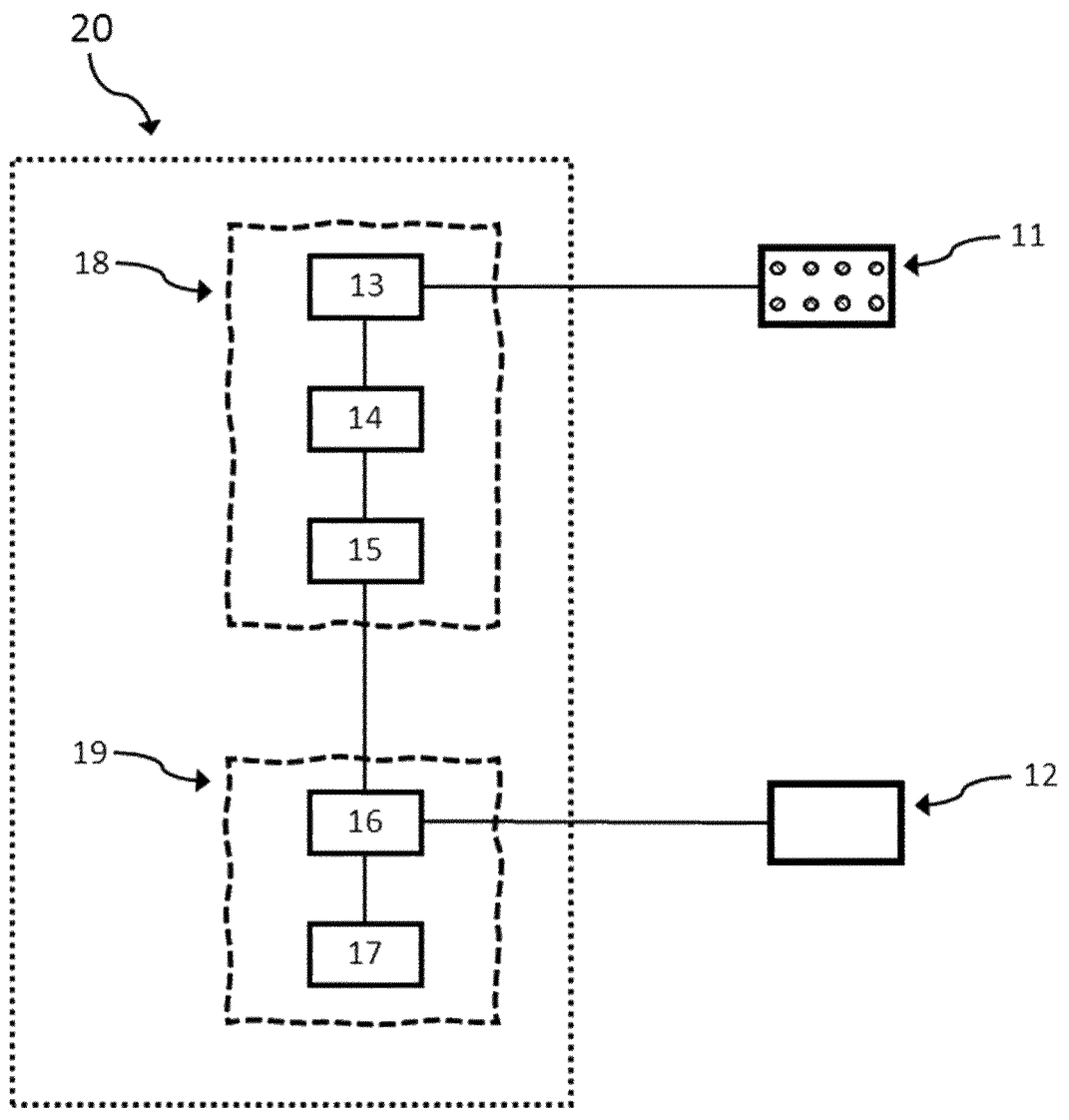
FIG. 4 shows a schematic representation of an exemplary probe as described herein.

A schematic representation of an exemplary probe as defined herein is given in FIG. 4. Respective potentials and consequently voltages of the conductive elements of electrode array (11) are obtained by measuring device (13). Data analysis device (14) then identifies deviating conductive elements and/or entire electrode array and calculates an average reference voltage for the non-deviating conductive elements of the electrode array (11), which are then used by current controller (15) to optionally initiate a re-calibration or restoring of any one or more deviating conductive element. On basis of the average reference voltage provided by the data analysis device and the potential/voltage obtained from the sensing electrode (12), calculation device (16) then determines a value for the ion concentration and transmits such value to output device (17).

As indicated in FIG. 4, measuring device (13), data analysis device (14), and current controller (15) may be comprised in a reference electrode controller (18). Equally, calculation device (16) and output device (17) may be comprised in a sensing electrode controller (19). Both, reference electrode controller (18) and sensing electrode controller (19) may then be comprised in a probe controller (20). Alternatively, it is equally possible to comprise measuring device (13), data analysis device (14), calculation device (16), and output device (17) in a single device, possibly but not necessarily further comprising reference electrode controller (15).

The present probe and/or reference electrode may be used to determine ion concentrations in, preferably aqueous, solution. Such method of determining an ion concentration in, preferably aqueous, solution comprises the steps of (a) providing an electrode array, a junction element, a measuring device, and connecting means, all as defined herein;

(b) (b') submersing the electrode array and the junction element in a liquid, preferably in an aqueous medium, and connecting it to the measuring device; or (b") submersing the electrode array connected to the measuring device in a liquid, preferably in an aqueous medium;

(c) obtaining a voltage value for each of the conductive elements comprised in the electrode array by using the measuring device; and (d) performing statistical analysis of the voltage values obtained in step (c) to identify any deviating conductive element, and to calculate an average reference voltage, wherein steps (a), (b), (c), and (d) are performed in sequential order.

For determining the ion concentration in a liquid, preferably in an aqueous medium, the herein defined electrode array is submersed in the liquid and then connected to the measuring device, or alternatively the electrode array may first be connected to the measuring device and then, i.e. already connected to the measuring device, submersed in a liquid, preferably an aqueous medium. For reasons of user friendliness and assurance that the electrode array is well connected to the measuring device, it may be preferred for the electrode array to first be connected to the measuring device and then immersed in the liquid. Preferably, such submersing means that the entire electrode array is placed in the liquid such that the liquid covers all of the exposed surfaces of the conductive elements of the electrode array.

Irrespective of whether the electrode array is first connected and then submersed or the other way around, the electrode array is connected as described herein by connecting means.

The measuring device is then used to obtain a voltage value for each of the conductive elements comprised in the electrode array. For this, the measuring device receives a voltage value from each of the individual conductive elements in the electrode array. Such voltage values are then preferably stored or recorded, either non-permanently, such as in a memory chip, or permanently, such as on a hard drive.

The so-obtained voltage values are then used to perform a statistical analysis, identifying any deviating conducting element, and/or determine the average reference voltage of the electrode array, as described in detail in the following.

Any deviating conductive element—once identified—may either be switched off, either by the measuring device or by any other device capable and configured to do so, thus allowing for measurements using only non-deviant conductive elements.

It may also happen that due to the number of deviating conductive elements being too high, for example, being in total less than two, or, for example, having a too high average deviation for all of the conductive elements, the statistical analysis will not allow to determine an average reference voltage. In such a case the statistical analysis leads to the determination that the electrode array as a whole cannot be used for a meaningful and reliable measurement and may be declared deviating, i.e. unusable, in its entirety.

For an electrode array comprising only two conductive elements, the statistical analysis comprises comparing the voltages obtained, and if these differ substantially from each other, indicate both conductive elements, i.e. the entire electrode array in this case, as deviating or unusable for conducting the measurement.

For an electrode array comprising at least three conductive elements, such statistical analysis may be done by comparing the voltage of any individual element with the average voltage of the remaining elements, and if the voltage of the individual element differs substantially from the average of the remaining elements, indicate the respective individual conductive element as deviating.

Taking as a specific example an electrode array as described herein comprising three conductive elements CE1, CE2, and CE3 such statistical analysis may, for example, be done by comparing (i) the voltage for CE1 with the average voltage of CE2 and CE3, (ii) the voltage for CE2 with the average voltage of CE1 and CE3, and (iii) the voltage of CE3 with the average voltage of CE1 and CE2.

If then any of the individual voltage substantially differs from the average of the other two voltages, such individual voltage is then labeled deviating.

The statistical analysis is similarly conducted for electrode arrays comprising more than three conductive elements.

Alternatively, or in addition to such statistical analysis as described above, an average of the voltages of all conductive elements comprised in an electrode array as described above may be formed, and if a substantial error margin is detected the entire array indicated to be deviating, i.e. unusable for the immediate measurement to be conducted.

If the statistical analysis leads to the conclusion that the electrode array is usable, an average voltage is calculated on basis of the voltages obtained from the remaining, i.e. non-deviating, conductive elements. The so-calculated average voltage is in the following then used as the reference voltage.

Optionally, the user may be alerted to an entire electrode array or any conductive element(s) comprised in an electrode array to be deviating and/or unusable by, for example, sound, by a warning light, by a message displayed on a display, or any other suitable means.

For an entire electrode array deviating or unusable, the probe or electrode array controller preferably stops any on-going or to-be-done determination of an ion concentration.

Additionally, on basis of the results of the statistical analysis, i.e. whether any conductive elements are deviating or whether even the entire electrode array is unusable, a regeneration process may optionally be started either manually by the user or automatically. Such restitution process may be started immediately or at a pre-determined later time or at a user-determined later time. The reconstitution process may be applied to only the deviating conducting elements of an electrode array, or preferably to all conductive elements comprised in the electrode array, wherein deviating conductive elements have been identified, or in case the entire electrode array has been found unusable to all conductive elements of the electrode array.

The regeneration process is an electrochemical scrubbing and coating process. Such process preferably is done using de-halogenation/halogenation (e.g. de-chlorination/chlorination in case of potassium chloride being the electrolyte) the probe or electrode array controller may selectively apply a current to one or more conductive element or to all conductive elements of the electrode array. Preferably, a voltage of between 0.1 V and 10 V may be applied. Preferably, such voltage is applied for from 0.5 s to 60 s. For example, a current of 5 V may be applied for a duration of 30 s for strong chlorination, and for weaker chlorination a current of 1.3 V may be applied for a duration of 10 s. During the application of the current to the one or more conductive element, any suitable electrically conductive material, for example silver, preferably in form of a wire or a strip, may be used as an anode.

Alternatively to applying a current continuously for a certain length of time, it is also possible to provide such current in a pulsed sequence, i.e. several times for shorter periods of time, for example, until the performance of all conductive elements of the electrode array has been restored to working level.

In some instances a simple rinsing of the electrode array with water, preferably with deionized water, may already be sufficient to regenerate any deviating conductive element or electrode array.

The present probe and reference electrode as defined herein offer a number of advantages over the existing conventional probes and reference electrodes. The use of an electrode array as defined herein comprising at least two conductive elements allows to "self-test" the probe and/or reference electrode for correct functioning without the need for external calibration. In case an electrode array or any one or more of the conductive elements no longer functions correctly, the present electrode array or any one or more of the conductive elements may easily be restored to proper functional condition by allowing for easy scrubbing (cleaning) and restoring a clean metal surface of the conductive elements comprised in the electrode array.

In addition, the present probe and reference electrode may be stored in the dry state and can easily be put to use by simply immersing it with the junction element into water, thereby creating a stable and reproducible reference solution of a metal salt, preferably of potassium chloride.

Generally stated, the present probe and reference electrode, while surprisingly simple in construction, greatly reduces the amount of time and effort needed for maintenance, and at the same time allows to keep the accuracy and reliability expected from convention probes and reference electrodes.

It is also noted that the present probe and reference electrode offers a low-cost, environmentally friendly alternative to the conventional probes and reference electrodes still widely used today.

Further advantages are clearly evident from the description as well as the following examples, which are to illustrate the working of the present probe and reference electrode in a non-limiting way.

EXAMPLES

An electrode array (as shown in FIG. 1b) having a size of about 10 mm by 25 mm and being made of a non-conductive polymer comprising ten silver pellets as conductive elements was used to test and prove the feasibility of the present concept and to evaluate the advantages and the workings of the present probe and reference electrode.

Example 1

The electrode array comprising ten conductive pellet-shaped silver elements and a filter paper impregnated with potassium chloride were immersed in an aqueous medium and measured against a commercially available, conventional master reference electrode (Mettler Toledo LE438 with Ag/AgCl reference) in a simulation of a general workweek.

The conductive silver elements of the electrode array were (re) chlorinated or not at the start of each day as indicated in the following Table 1.

TABLE 1

| Start of day | Chlorination | Voltage [V] | Time [s] |
|---|---|---|---|
| 1 | Yes | 5 | 30 |
| 2 | Yes | 1.3 | 10 |
| 3 | Yes | 1.3 | 10 |
| 4 | Yes | 1.3 | 10 |

TABLE 1-continued

| Start of day | Chlorination | Voltage [V] | Time [s] |
|---|---|---|---|
| 5 | No | — | — |
| 6 | No | — | — |
| 7 | No | — | — |

It is noted that on day 3 during the day, two conductive elements were found to be deviating and were then regenerated through re-chlorinating by applying a voltage of 1.3 V for 10 s.

At the end of each day the junction element, i.e. the potassium chloride-impregnated filter paper, was removed and dried, and the electrode array rinsed with deionized water. Both, the electrode array and the junction element were then stored dry overnight. The subsequent re-humidification of the electrode array as well as of the junction elements were not found to affect performance of the conductive elements and the electrode array as a whole.

FIG. 5 shows the voltage curves for the ten conductive elements of the electrode array measured versus the reference electrode. It can clearly be seen that of the ten conductive elements comprised in the electrode array as described in the present application, only individual conductive elements start deviating or drifting at any given time. Expressed differently, the results show that the majority of conductive elements of the electrode array shows—at any given time—stable behavior. Hence, by disregarding voltages obtained from deviating conductive elements a reliable average voltage can be calculated and then used as reference value.

Example 2

In a further example the stability of the inter-element voltage, i.e. the voltage or potential difference, between the conductive elements of the electrode array was assessed for the present electrode array comprising ten conductive pellet-shaped silver elements and a filter paper impregnated with potassium chloride, both of which were immersed in an aqueous medium.

The top of FIG. 6 shows the voltage for each of the individual conductive elements comprised in the electrode array as described herein versus the average voltage of the remaining conductive elements.

The bottom of FIG. 6 shows the average voltage for the present electrode array with deviating conductive elements being disregarded.

From these results it can be concluded that deviating individual conductive elements can easily be identified, and—if the voltages obtained from such one or more deviating conductive elements are disregarded—a reliable reference voltage may be determined by taking the average voltage for the remaining (non-deviating) conductive elements.

In addition, the graph of FIG. 6 shows that generally when the number of deviating conductive elements is more than half the total number of the conductive elements comprised in the present electrode array, the average voltage so-calculated becomes less reliable as can be seen in FIG. 6 in that the respective values vary randomly with time.

The examples further allowed to determine that a replacement of the junction element, i.e. the potassium chloride-impregnated patent strip, was easily possible without visibly affecting performance and stability of the present probe and electrode array.

It is also noted that the 15 mm wide paper strips used in the example had an electrical resistance of 1.8 to 2.1 kΩ, found to be on the same order of magnitude as the resistance of the porous junction of the conventional master reference electrode. Since the resistance of an ISFET is at least several GΩ, the present electrode resistance is considered to be well suited to measure ion concentrations, e.g. pH, in combination with an ISFET.

The experiments of Example 1 also confirmed that no visible general drift in the electrode array and the respective conductive elements occurred over the course of a day, indicating—without wishing to be bound by theory—that the number of chloride ions released from the potassium chloride-impregnated paper strip remained on the same level throughout the whole day.

Example 3

A probe comprising the electrode array and as junction element the potassium chloride-impregnated paper strip as used in Examples 1 and 2 was used in combination with a commercially available ISFET pH-sensor (MICROSENS MSFET 3330 pH sensor, available from MICROSENS S.A., EPFL Innovation Part, Batiment D, 1015 Lausanne, Switzerland). Comparative measurements were conducted using the above-mentioned commercially available, conventional master reference electrode (Mettler Toledo LE438 with Ag/AgCl reference) in combination with the above-mentioned commercially available ISFET pH sensor.

The conductive elements of the electrode array were connected to a measuring device as described herein and re-chlorinated by applying a voltage of 5 V for 30 s.

The ISFET was then dipped in aqueous reference media of having pH-values of 7.0, 4.0, and 10.00, respectively.

Figure 7:
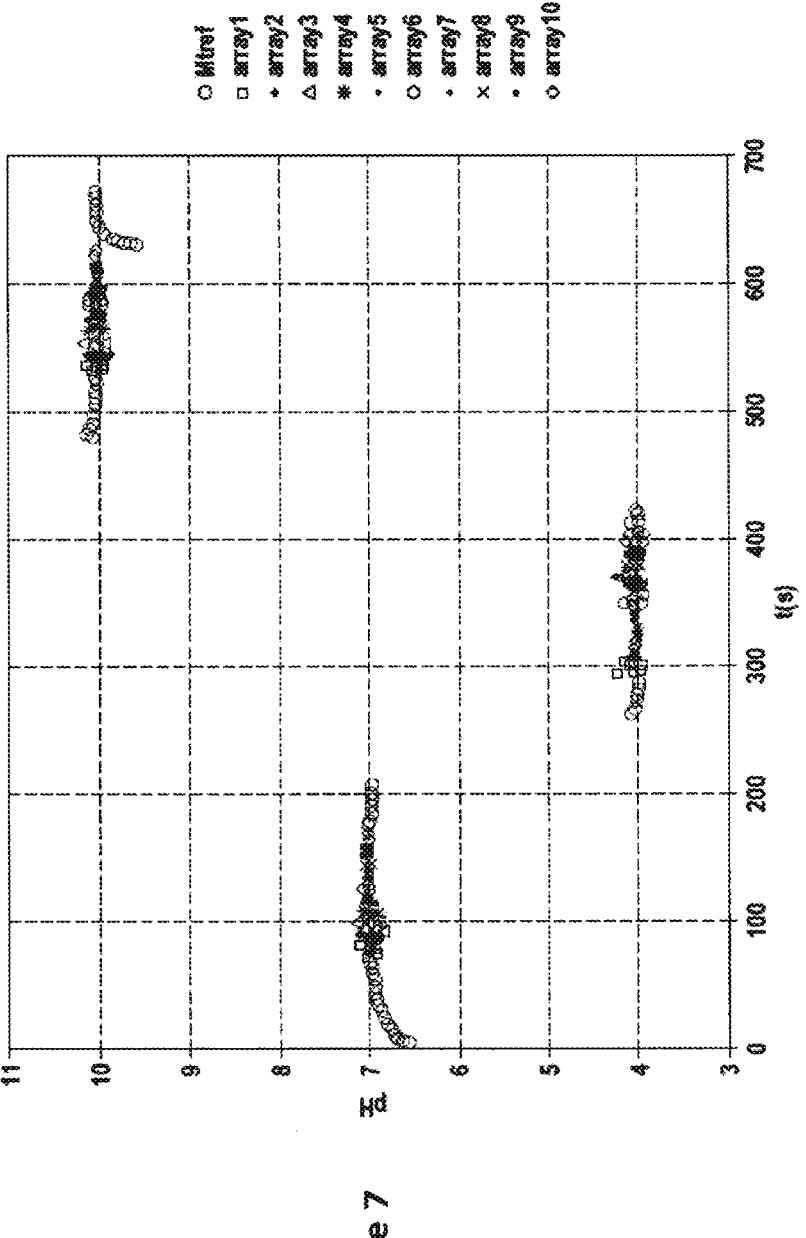
FIG. 7 shows the results for Example 3, wherein the pH of three different aqueous media was determined using as reference an electrode array as described herein or a conventional reference electrode.

The results are shown in FIG. 7. It can clearly be seen that for all of the conductive elements of the electrode array as well as for the convention reference electrode the same values were obtained within the error margins of the measurement.

Thus, the results obtained herein clearly show the usefulness and the advantages of the present probe and electrode array. The present probe and electrode array surprisingly allow for a very simple, cost-efficient but at the same time very reliable and easy-to-use reference electrode for the determination of ion concentrations in aqueous medium.

Generally stated, the present probe and reference electrode offer numerous advantages in respect to conventional probes and reference electrodes, as the skilled person can easily determine from the present description and examples.

The present inventors were quite surprised to find that the individual conductive elements of the electrode array do not start to shift/drift simultaneously but that it is rather individual conductive elements that show deviating behavior. Relatively simple statistical analysis of the respective voltages obtained for the respective conductive elements of the electrode array allow identifying such deviating conductive elements, and then take corrective action, such as for example disregarding the measured values provided by such deviating conductive element or regenerating such deviating conductive elements by applying a voltage to re-chlorinate the surface of such element, which can also be done with the respective probe or reference electrode remaining in place, i.e. without for example having to remove the junction element comprising the electrolyte.

This also illustrates that the present probe and reference electrode are characterized by being very easy to maintain and keep in such condition that reliable and meaningful results may be obtained. In comparison to the conventionally used reference electrode, such as the calomel electrode, the present probe and reference electrode may be stored in dry state and can then easily be put into use in an aqueous medium by simply bringing the junction element comprising the electrolyte into proximity of the conductive elements of the present electrode array. It is no longer necessary to store the present electrode array submersed in an aqueous solution of an electrolyte as described herein but offers the great advantage that it can be stored in dry state, even for longer periods.

As the good and reliable functioning of the present probe and electrode can easily be monitored by electronic circuitry, the continuous presence of an operator is no longer necessary, thereby also offering significant potential for automation.

Thus, the present probe and reference electrode generally allows for any one or more of the following preferred modes of operation:

Rinsing, preferably with deionized water;

dry storage, also over longer periods of time;

mounting a junction element comprising a porous material, such as an electrolyte-soaked filter paper, in proximity to the conductive elements as defined herein;

performing a stability assessment by inter-element voltage measurement;

usage in the determination of ion concentrations, including pH-measurements, in aqueous medium, thereby allowing to exclude deviating conductive elements; and restoring stability for deviating conductive elements or entire electrode arrays by manual or automatic galvanic di-chlorination and re-chlorination of conductive elements.

It has actually come as a great surprise to the present inventors that all of these advantages could be achieved by a probe and reference electrode with such a surprisingly simple and/or easy-to-produce design.

REFERENCE NUMERALS

1 Electrode array
2 Supporting base
3 Conductive element(s)
4 Junction element
5 Side wall(s)
6 Connecting means
7 Measuring device
11 Electrode array
12 Sensing electrode
13 Measuring device
14 Data analysis device
15 Current controller
16 Calculation device
17 Output device
18 Reference electrode controller
19 Sensing electrode controller
20 Probe controller

The invention claimed is:

1. A probe for potentiometric measurements, the probe comprising (i) an electrode array comprising at least two conductive elements electrically isolated against each other each of said at least two conductive elements having an exposed conductive surface;

(ii) a junction element comprising an absorbent material and an electrolyte, connecting the conductive surface of said conductive elements to a liquid;

(iii) a measuring device capable of measuring voltages between the conductive elements comprised in the electrode array; and (iv) connecting means for connecting the electrode array and the measuring device;

wherein the electrode array is immersed in an aqueous solution of the electrolyte.

2. The probe according to claim 1, wherein the electrode array comprises at least three and at most twelve conductive elements.

3. The probe according to claim 1, wherein the conductive elements comprise a conductive material selected from the group consisting of silver, gold, platinum, mercury, carbon, and any blend thereof.

4. The probe according to claim 1, wherein the conductive elements are pellet-shaped.

5. The probe according to claim 1, wherein the absorbent material is either a porous material.

6. The probe according to claim 1, wherein the electrolyte is an alkaline metal chloride.

7. The probe according to claim 1, wherein the measuring device is an electronic circuitry which is connected to and measuring voltage between the conductive elements.

8. The probe according to claim 7, wherein the electronic circuitry is able to selectively address any one or more individual conductive elements, and/or to selectively apply a current to any one or more individual conductive element.

9. The probe according to claim 1, wherein the probe further comprises a controller unit that (i) controls the electronic circuitry, (ii) is capable of connecting and/or addressing the conductive elements either singly or in any combination, and (iii) is capable of identifying unstable conductive elements in the electrode array.

10. The probe according to claim 9, wherein the controller eliminates unstable conductive elements in the electrode array by selectively applying current with selected polarity to at least one of said unstable conductive elements for electrochemical scrubbing and coating.

11. The probe according to claim 1, further comprising an electrochemical sensor, the electrochemical sensor being an ion-sensitive field-effect transistor (ISFET).

12. A vessel or conduit comprising the probe of claim 1.

13. A system comprising the vessel of claim 12, said system being selected from the group consisting of water purification system and water solution preparation system.

14. A method of determining an ion concentration in solution, the method comprising in sequential order the steps of (a) providing an electrode array comprising at least two conductive elements electrically isolated against each other each of said at least two conductive elements having an exposed conductive surface; a junction element comprising an absorbent material and an electrolyte; a measuring device capable of measuring voltages between the conductive elements comprised in the electrode array; and connecting means for connecting the electrode array and the measuring device;

(b) (b') submersing the electrode array and the junction element in a liquid and connecting it to the measuring device; or (b") submersing the electrode array connected to the measuring device in a liquid;

(c) obtaining a voltage value for each of the conductive elements comprised in the electrode array by using the measuring device; and (d) performing statistical analysis of the voltage values obtained in step (c) to identify any deviating conductive element, and to calculate an average reference voltage, wherein steps (a), (b), (c), and (d) are performed in sequential order.

15. The method according to claim 14, further comprising the steps of (h) performing a statistical analysis determining the stability of the array and its individual elements by analyzing the voltage readings obtained in claim 14 (b) by using a controller; and (i) if it is determined that there is at least one unstable conductive element, selectively applying current with selected polarity to such at least one deviating conductive element for electrochemical scrubbing and coating.

16. A method of determining an ion concentration in solution, the method comprising in sequential order the steps of (a) providing an electrode array comprising at least two conductive elements electrically isolated against each other each of said at least two conductive elements having an exposed conductive surface; a junction element comprising an absorbent material and an electrolyte; a measuring device capable of measuring voltages between the conductive elements comprised in the electrode array; and connecting means for connecting the electrode array and the measuring device;

(b) (b') submersing the electrode array and the junction element in a liquid and connecting it to the measuring device; or (b") submersing the electrode array connected to the measuring device in a liquid;

(c) obtaining a voltage value for each of the conductive elements comprised in the electrode array by using the measuring device; and (d) performing statistical analysis of the voltage values obtained in step (c) to identify any deviating conductive element, and to calculate an average reference voltage, wherein steps (a), (b), (c), and (d) are performed in sequential order; said method further comprising (e) providing an electrochemical sensor that is an ion-sensitive field-effect transistor in an aqueous ion solution;

(f) subsequently taking a voltage measurement from the electrochemical sensor; and (g) using a calculation device to determine the ion concentration on basis of the average reference voltage obtained in step (d) and the voltage measurement of step (f), wherein steps (a) to (f) may be performed in any order provided that (i) steps (a) to (d) are performed sequentially;

(ii) steps (f) and (g) are performed sequentially; and (iii) step (g) is performed after any of steps (a) to (f).

* * * * *